(12) United States Patent
Bonutti et al.

(10) Patent No.: US 7,955,286 B2
(45) Date of Patent: Jun. 7, 2011

(54) ELBOW ORTHOSIS

(75) Inventors: Boris P. Bonutti, Effingham, IL (US);
Peter M. Bonutti, Effingham, IL (US);
Kevin R. Ruholl, Effingham, IL (US);
Glen A. Phillips, Effingham, IL (US)

(73) Assignee: Bonutti Research Inc., Effingham, IL (US)

( * ) Notice: Subject to any disclaimer, the term of this patent is extended or adjusted under 35 U.S.C. 154(b) by 325 days.

(21) Appl. No.: 11/687,679

(22) Filed: Mar. 19, 2007

(65) Prior Publication Data
US 2007/0219476 A1 Sep. 20, 2007

Related U.S. Application Data

(60) Provisional application No. 60/783,895, filed on Mar. 20, 2006.

(51) Int. Cl.
*A61F 5/00* (2006.01)
(52) U.S. Cl. .............................. 602/16; 602/20; 602/23
(58) Field of Classification Search ................ 602/5, 16, 602/20–27; 128/881, 882
See application file for complete search history.

(56) References Cited

U.S. PATENT DOCUMENTS

| 5,503,619 | A |   | 4/1996  | Bonutti |         |
|-----------|---|---|---------|---------------|---------|
| 5,611,764 | A |   | 3/1997  | Bonutti et al. |         |
| 5,683,351 | A | * | 11/1997 | Kaiser et al. | 601/40  |
| 5,848,979 | A | * | 12/1998 | Bonutti et al. | 601/5   |
| 5,951,499 | A | * | 9/1999  | Saringer et al. | 601/33 |
| 6,146,341 | A | * | 11/2000 | Sato et al.   | 601/23  |
| 6,502,577 | B1 |  | 1/2003  | Bonutti       |         |
| 2005/0197605 | A1 | * | 9/2005 | Bonutti et al. | 602/5 |

OTHER PUBLICATIONS

European Patent Office, Search Report and Opinion of Application No. 07758851.5-2310, Feb. 5, 2010, 6 pages, EP.

* cited by examiner

*Primary Examiner* — Michael A. Brown
(74) *Attorney, Agent, or Firm* — Armstrong Teasdale LLP

(57) ABSTRACT

An orthosis for stretching tissue around a joint of a patient between first and second relatively pivotable body portions. The orthosis includes a first arm member affixable to the first body portion and including a first extension member extending therefrom. A second arm member affixable to the second body portion is also included and has a second extension member having an arcuate shape extending therefrom. A third arm member including a third extension member having an arcuate shape extending therefrom is interposed between the first and second arm members. The third arm member is operatively connected to the first and second arm members, such that the first and third arm members travel along an arcuate path defined by the second extension member when the third arm member is moved from a first position to a second position relative to the second arm member. Furthermore, the first arm member can slide along the third extension member as the third arm member is moved from the first position to the second position relative to the second arm member.

33 Claims, 16 Drawing Sheets

ELBOW ORTHOSIS

CROSS-REFERENCE TO RELATED APPLICATION

The present application claims priority to U.S. Provisional Patent Application No. 60/783,895 filed Mar. 20, 2006, entitle ELBOW ORTHOSIS, the contents of which are herein incorporated by references in its entirety

FIELD OF THE INVENTION

The present invention relates to an adjustable orthosis for stretching tissue in the human body. In particular, the present invention relates to an adjustable orthosis which can be used for stretching tissue such as ligaments, tendons or muscles around a joint during flexion or extension of the joint.

BACKGROUND OF THE INVENTION

In a joint, the range of motion depends upon the anatomy of that joint and on the particular genetics of each individual. Typically, joints move in two directions, flexion and extension. Flexion is to bend the joint and extension is to straighten the joint; however, in the orthopedic convention some joints only flex. For example, the ankle has dorsiflexion and plantarflexion. Other joints not only flex and extend, they rotate. For example, the elbow joint has supination and pronation, which is rotation of the hand about the longitudinal axis of the forearm placing the palm up or the palm down.

When a joint is injured either by trauma or by surgery, scar tissue can form, often resulting in flexion or extension contractures. Such conditions can limit the range of motion of the joint, limiting flexion (in the case of an extension contracture) or extension (in the case of a flexion contracture) of the injured joint. It is often possible to correct this condition by use of a range-of-motion (ROM) orthosis.

ROM orthoses are devices commonly used during physical rehabilitative therapy to increase the range-of-motion over which the patient can flex or extend the joint. Commercially available ROM orthoses are typically attached on opposite members of the joint and apply a torque to rotate the joint in opposition to the contraction. The force is gradually increased to increase the working range or angle of joint motion. Exemplary orthoses include U.S. Pat. No. 6,599,263, entitled "Shoulder Orthosis;" U.S. Pat. No. 6,113,562, entitled "Shoulder Orthosis;" U.S. Pat. No. 5,848,979, entitled "Orthosis;" U.S. Pat. No. 5,685,830, entitled "Adjustable Orthosis Having One-Piece Connector Section For Flexing;" U.S. Pat. No. 5,611,764, entitled "Method of Increasing Range of Motion;" U.S. Pat. No. 5,503,619, entitled "Orthosis for Bending Wrists;" U.S. Pat. No. 5,456,268, entitled "Adjustable Orthosis;" U.S. Pat. No. 5,453,075, entitled "Orthosis with Distraction through Range of Motion;" U.S. Pat. No. 5,395,303, entitled "Orthosis with Distraction through Range of Motion;" U.S. Pat. No. 5,365,947, entitled "Adjustable Orthosis;" U.S. Pat. No. 5,285,773 entitled "Orthosis with Distraction through Range of Motion;" U.S. Pat. No. 5,213,095, entitled "Orthosis with Joint Distraction;" and 5,167,612, entitled "Adjustable Orthosis," all to Bonutti and herein are expressly incorporated by reference in their entirety.

SUMMARY OF THE INVENTION

The present invention provides an orthosis for stretching tissue around a joint of a patient between first and second relatively pivotable body portions. The joint and the first and second body portions define on one side of the joint an inner sector which decreases in angle as the joint is flexed and define on the opposite side of the joint an outer sector which decreases in angle as the joint is extended.

The orthosis includes a first arm member affixable to the first body portion. The first arm member has a first extension member extending therefrom. A second arm member affixable to the second body portion is also included. The second arm member has a second extension member having an arcuate shape extending therefrom. A third arm member including a third extension member, having an arcuate shape extending therefrom, is interposed between the first and second arm members. The second and third arm members are operatively connected, such that the third arm member travels along an arcuate path defined by the second extension member when the third arm member is moved from a first position to a second position relative to the second arm member. The first arm member is slidingly connected to the third extension member, such that the first arm member slides along an arcuate path defined by the third extension member when the third arm member is moved from the first position to the second position relative to the second arm member.

The orthosis further includes a drive assembly for selectively moving the third arm member relative to the second extension member. The drive assembly is mounted onto the third arm member, engaging the second extension member. The drive assembly can be manually or automatically actuated to selectively move the third arm member relative to the second extension member.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention relates to an orthosis for moving a joint between first and second relatively pivotable body portions. The joint and the first and second body portions define on one side (the flexor side) of the joint an inner sector which decreases in angle as the joint is flexed (bent) and on the opposite side (the extensor side) of the joint an outer sector which decreases in angle as the joint is extended (straightened). The orthosis of the present invention is affixable to either the flexor or extensor side of the joint for treatment of flexion or extension contractures.

Figure 1:
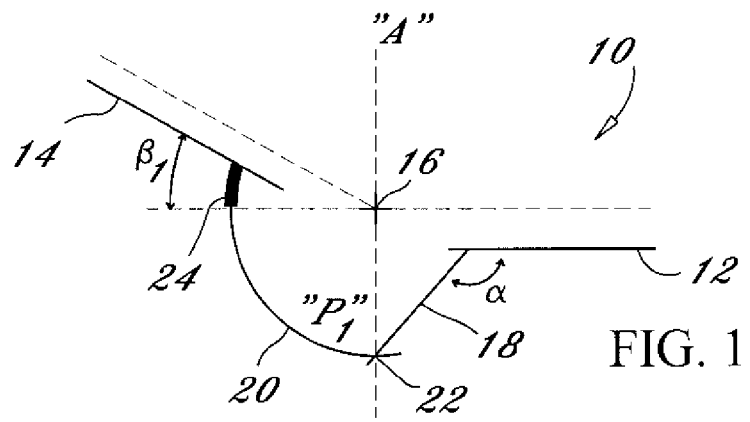
FIG. 1 is a schematic diagram of the orthosis of the present invention in a flexed position.

Referring now to the drawing figures in which like reference designators refer to like elements, there is shown in FIG. 1, a schematic of the orthosis 10 of the present invention. The orthosis 10 includes a first arm member 12 attachable to the first body portion and a second arm member 14 attachable to the second body portion, wherein a joint axis of rotation 16 is interposed between and offset from the first and second arm members 12 and 14. The first and second arm members 12 and 14 are operatively connected to each other offset from the joint axis 16.

The first arm member 12 of the orthosis 10 includes a First extension member 18, which extends at angle $\alpha$ from the first arm member 12. The second arm member 14 of the orthosis 10 includes a second extension member 20 extending therefrom and having an arcuate shape. The first and second extension members 18 and 20 are operatively connected at point "P," such that in operation the second extension member 20 travels along an arcuate path about and substantially through point "P." The arcuate shape of the second extension member 20 results in the second body portion rotating about the joint axis 16, when the second arm member 14 is moved from a first position to a second position relative to the first arm member 12. The angle $\alpha$ between the first extension member 18 and the first arm member 12 and the radius of curvature of the second extension member 20 are a function of the joint to be treated and the degree of flexion or extension contractures.

The orthosis further includes a drive assembly 22 at point "P." The drive assembly connects the first and second extension members 18 and 20 for applying force to the first and second arm members 12 and 14 to pivot the first and second body portions relative to each other about the joint.

Figure 2:
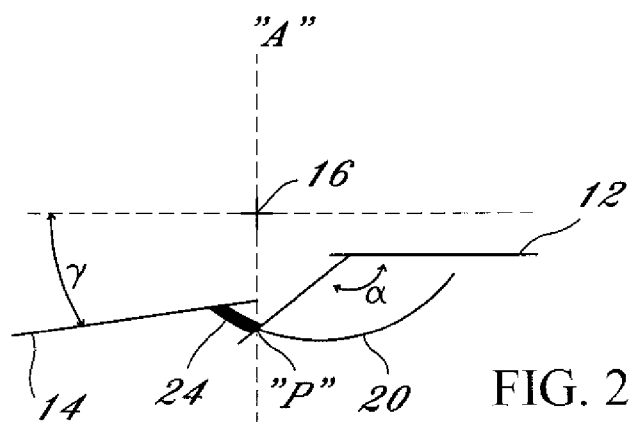
FIG. 2 is a schematic diagram of the orthosis of the present invention in an extended position.

The orthosis 10 of the present invention is shown having an angle $\alpha$ such that the operative connection, at point "P" of the first and second extensions 18 and 20 is located in a plane "A" passing through the joint axis 16, wherein plane "A" is substantially orthogonal to a longitudinal axis of the first arm member 12. Plane "A" can also be referred to as an orthosis plane. This position of point "P" provides an angle $\beta_1$ between the second arm member 14 and the joint axis 16, wherein $\beta_1$ is the maximum angle of flexion. As shown in FIG. 2, the second extension member includes a stop 24. The stop 24 acts to limit the angle of maximum extension $\gamma$ between the second arm member 14 and the joint axis 16. An increase in the length of the stop 24 will decrease the angle of maximum extension $\gamma$. A decrease in the length of the stop 24 will increase the angle of maximum extension $\gamma$.

Figure 3:
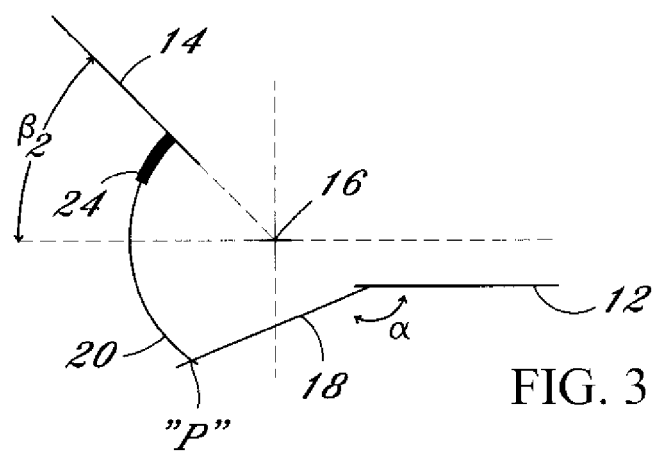
FIG. 3 is a second schematic diagram of the orthosis of the present invention in a flexed position.

Referring to FIG. 3, the maximum flexion angle can be increased by increasing the angle $\alpha$. An increase in the angle $\alpha$ will move the point "P" to a location "in front of" the plane "A." This position of point "P" provides an angle $\beta_2$ between the second arm member 14 and the joint axis 16 in maximum flexion, wherein $\beta_2$ is greater than $\beta_1$. The greater the angle $\alpha$, the greater the angle of maximum flexion.

Alternatively, (not shown) a decrease in the angle $\alpha$ will move the point "P" to a location "behind" the plane "A." This position of point "P" provides an angle $\beta_3$ between the second arm member 14 and the joint axis 16 in maximum flexion, wherein $\beta_3$ is less than $\beta_1$. The smaller the angle $\alpha$, the smaller the angle $\beta$ of maximum flexion.

Figure 4:
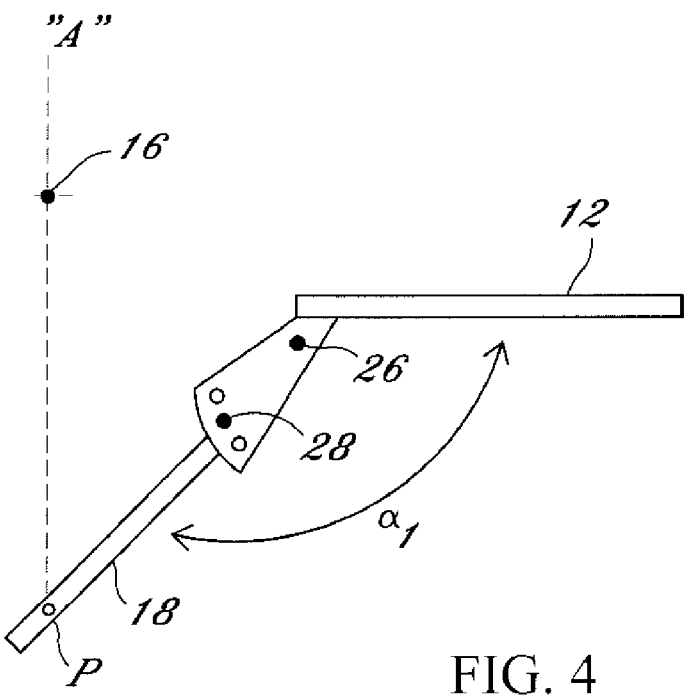
FIG. 4 shows an adjustable first extension member of the orthosis of the present invention.

Referring to FIG. 4, the first extension member 18 is selectively, pivotally connected at location 26 to the first arm member 12. The pivotal connection 26 of the first extension member 18 permits the angle $\alpha$ between the first extension member 18 and the first arm member 12 to be selectively increased and decreased, increasing and decreasing the range of motion. In a first position 28, the first extension member 18 is positioned at an angle $\alpha_1$, wherein the operative connection, at point "P," of the first and second extension members 18 and 20 is located in a plane "A" passing through the joint axis 16, wherein plane "A" is substantially orthogonal to a longitudinal axis of the first arm member 12. The first position 28 of point "P" provides a maximum angle of flexion of $\beta_1$. The second extension member stop 24 acts to limit the angle of maximum extension $\gamma_1$ between the second arm member 14 and the joint axis 16.

Figure 5:
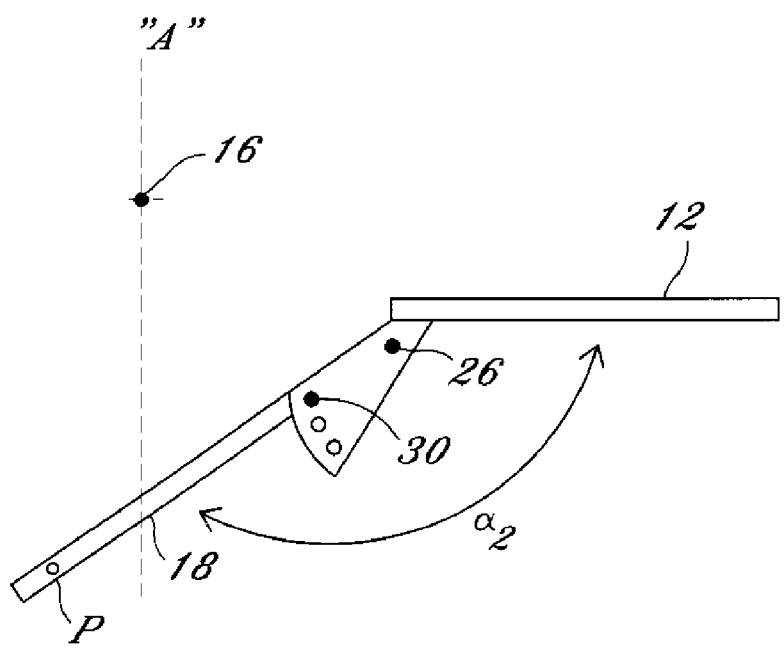
FIG. 5 shows the adjustable first extension member of FIG. 4 in a second position.

Referring to FIG. 5, in a second position 30 the angle $\alpha$ is increased to an angle $\alpha_2$, positioning the point "P" to a location "in front of" the plane "A." The second position 30 of point "P" provides a maximum angle of flexion of $\beta_2$, wherein $\beta_2$ is greater than $\beta_1$. The second extension member stop 24 acts to limit the angle of maximum extension $\gamma_2$ between the second arm member 14 and the joint axis, wherein $\gamma_2$ is less the $\gamma_1$.

The selective pivotal connection 26 of the first extension member 18 to the first arm member 12 can have a plurality of selectable positions. The angle $\alpha$ between the first arm member 12 and the first extension 18 can be selectively increased to move the point "P", on, "in front of" or "behind" the plane "A." It is also envisioned that a positioned can be selected to increase the angle $\alpha$ between the first arm member 12 and the first extension 18 sufficiently to move the point "P" "in front of" plane "A" and "above" the longitudinal axis of the first arm member 12, maximizing the maximum angle of flexion $\beta$.

The orthosis 10 of the present invention can be connected to the flexor side of the first and second body portions of the joint, which results in a decrease in angle as the joint is flexed (bent) and an increase in angle and the joint is extended (straightened). Alternatively, orthosis 10 of the present invention can be connected to the extensor side of the joint, which results in a decrease in angle as the joint is extended straightened and an increase in angle as the joint is flexed (bent).

Figure 6:
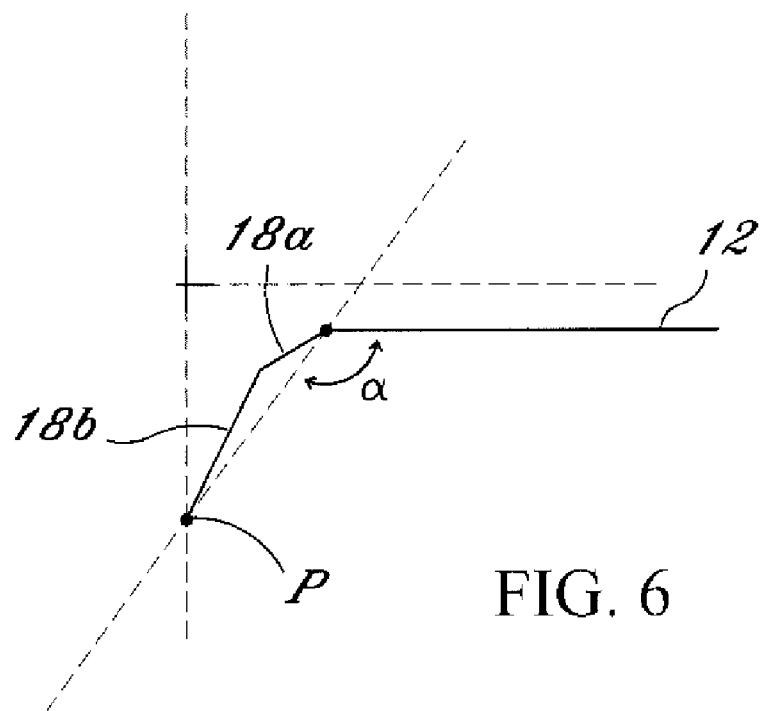
FIG. 6 shows a segmented first extension member of the present invention.
Figure 7:
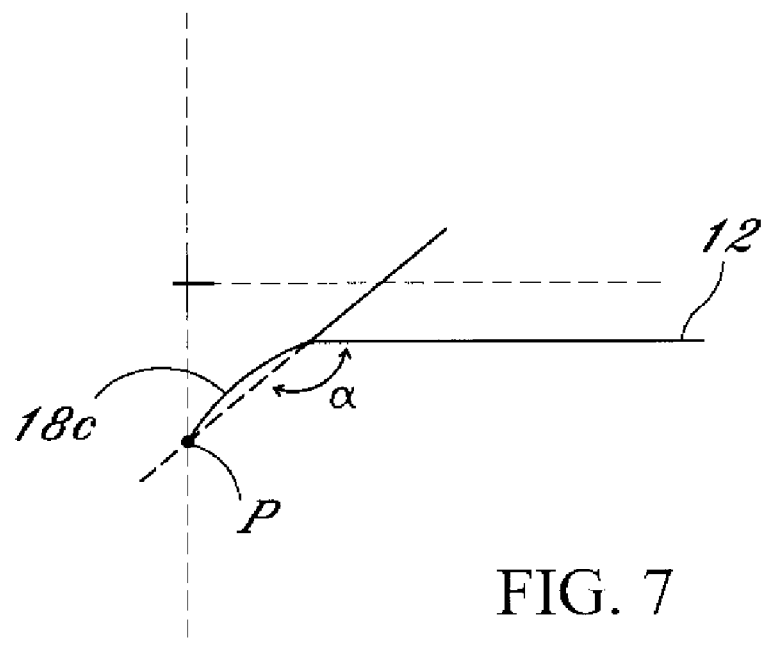
FIG. 7 shows an arcuate first extension member of the present invention.

The previous description of the first arm member 12 depicts a first extension 18 having a substantially linear shape, extending at an angle $\alpha$ from the first arm member 12. However, it is within the scope of the present invention that the first extension member 18 can be any shape extending from the first arm member 12 which positions the point "P" in the desired relationship to the plane "A." Referring to FIG. 6, a segmented fist extension member is shown, including a first extension member segment 18*a* and a second extension member segment 18*b*. The first and second extension member segments 18*a* and 18*b* extend from the first arm member 12, positioning the point "P" at an angle α from the first arm member 12. Referring to FIG. 7, an arcuate first extension member 18*c* is shown. The arcuate extension member 18*c* extends from the first arm member 12, positioning the point "P" at an angle α from the first arm member 12.

Figure 8:
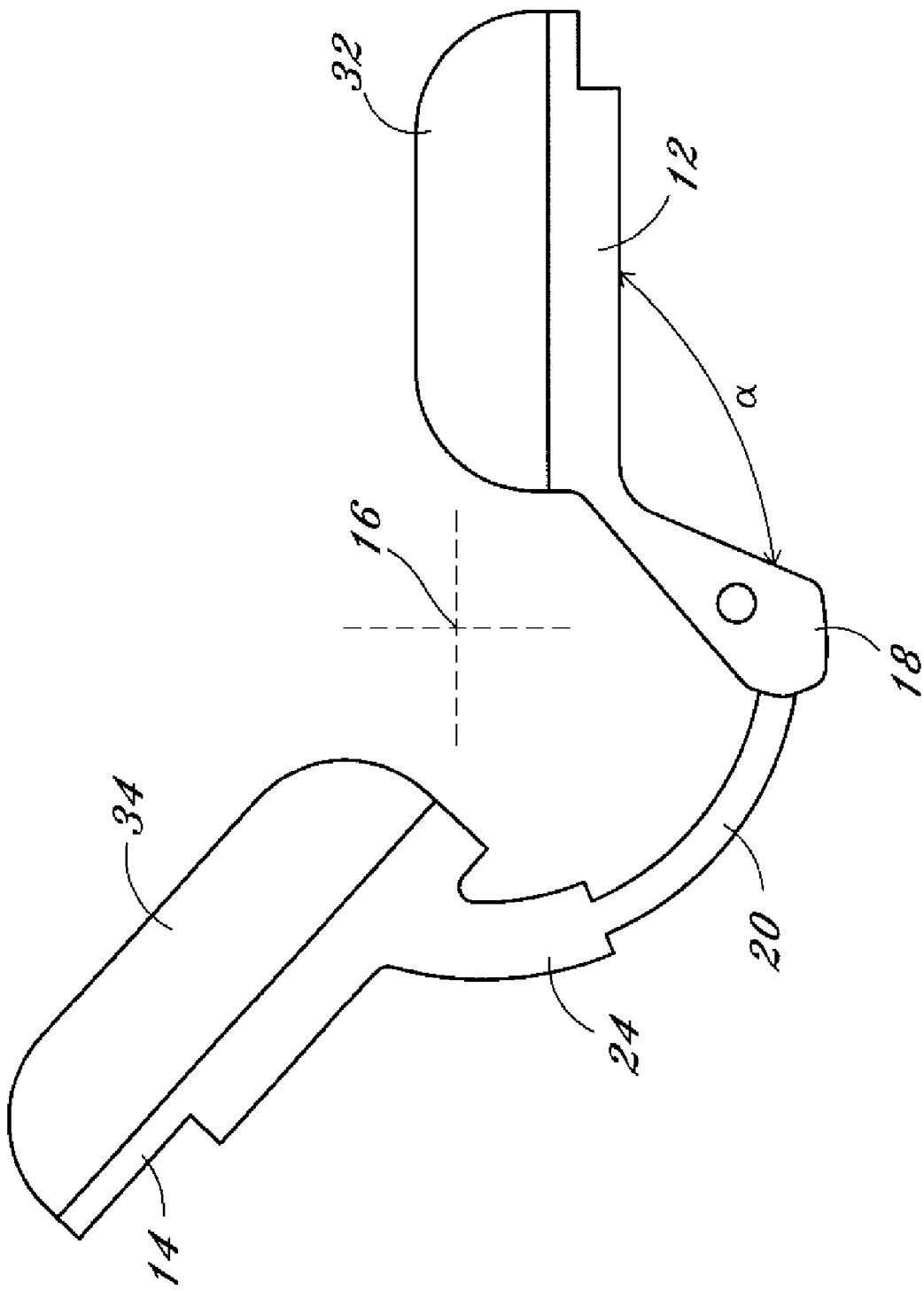
FIG. 8 shows an orthosis of the present invention.

Referring to FIG. 8, the orthosis 10 of the present invention includes a first arm member 12 attachable to the first body portion and a second arm member 14 attachable to the second body portion, wherein the joint axis 16 is interposed between and offset from the first and second arm members 12 and 14. The first and second arm members 12 and 14 are connected with each other offset from the joint axis 16.

The first arm member 12 of the orthosis 10 includes a first extension member 18, which extends at angle α from the first arm member 12. The second arm member 14 of the orthosis 10 includes a second extension member 20, having an arcuate shape. The first and second extension members 18 and 20 are operatively connected a point "P," such that in operation the second extension member 20 travels along an arcuate path about and substantially through point "P." The arcuate shape of the second extension member 20 results in the second body portion rotating about the joint axis 16, when the second arm member 14 is moved from a first position to a second position relative to the first arm member 12. The angle α between the first extension member 18 and the first arm member 12 and the radius of curvature of the second extension member 20 are a function of the joint to be treated and the degree of flexion or extension contractures.

A first cuff 32 is attached to the first arm member 12, wherein the first cuff 32 is positionable about the first body portion. The first cuff 32 is attached to the first body portion by cuff straps. The first cuff 32 secures the first body portion to the first arm member 12. A second cuff 34 is attached to the second arm member 14, wherein the second cuff 34 is positionable about the second body portion. The second cuff 34 is attached to the second body portion by cuff straps. The second cuff 34 secures the second body portion to the second arm member 14. (The term "cuff" as used herein means any suitable structure for transmitting the force of the orthosis 10 to the limb portion it engages.)

In an exemplary use, the orthosis 10 is operated to extend a joint in the following manner. The first cuff 32 is fastened about the first body portion tightly enough that the first arm member 12 may apply torque to the first body portion without having the first cuff 32 slide along the first body portion. Similarly, the second cuff 34 is fastened securely around the second body portion so that the second arm member 14 may apply torque to the second body portion without the second cuff 34 sliding along the second body portion. The orthosis 10 is attached to the first and second body portions in a first position. The second arm member 14 is rotated from the first position to a second position, relative to the first arm member 12, rotating the second body portion about the joint axis 16 stretching the joint. As the second arm member 14 is rotated to the second position, the second extension member 20 travels along an arcuate path about and substantially through point "P." The orthosis 10 is maintained in the second position for a predetermined treatment time providing a constant stretch to the joint. The orthosis 10 may alternatively be configured to impart a constant force or load on the joint or may utilize the techniques of Static Progressive Stretch as described in co-pending application Ser. No. 11/203,516, entitled "Range of Motion System and Method", and filed on Aug. 12, 2005, the entirety of which is incorporated by reference.

Additionally, the second extension member 12 can be made of a substantially rigid but flexible material, such that while the second extension member 12 is in the second position, the second extension member 12 acts like a spring, providing dynamic stretch to the connective tissue of the joint.

After the expiration of the treatment time, the second arm member 14 is moved back to the first position, relieving the joint. Optionally, the second arm member 14 can be rotated to a third position, increasing the stretch on the joint. The second arm member 14 can be rotated at discrete time intervals to incrementally increase the stretch of the joint through the treatment cycle. After completion of the treatment cycle, the second arm member is returned to the first position for removal of the orthosis 10.

The first and second arm members 12 and 14 are rigid members made of, for example, aluminum. stainless steel, polymeric, or composite materials. The arms are rigid so as to be able to transmit the necessary forces. It should be understood that any material of sufficient rigidity can be used.

In an embodiment, the components of the orthosis 10 of the present invention are made by injection molding. Generally for injection molding, tool and die metal molds of the orthosis 10 components are prepared. Hot, melted plastic material is injected into the molds. The plastic is allowed to cool, forming components. The components are removed from the molds and assembled. The cuff portions 32 or 34 can be individual molded and attached to the arm members 12 or 14. Alternatively, the cuff portions can be molded as an integrated part of the arm members 12 or 14.

In use, the orthosis 10 can be connected to the flexor side of the first and second body portions of the joint, which results in a decrease in angle as the joint is flexed (bent) and an increase in angle as the joint is extended (straightened). Alternatively, orthosis 10 of the present invention can be connected to the extensor side of the joint, which results in a decrease in angle as the joint is extended straightened and an increase in angle as the joint is flexed (bent).

In an embodiment, the orthosis 10 includes a first cuff 32 for attachment to a first body portion, and a second cuff 34 for attachment to a second body portion. The first body portion is joined to the second body portion at a joint, around which is located, as is well known, soft tissue. Each of the first and second cuffs 32 and 34 includes loop connectors for receiving straps extending around the body portions to clamp the cuffs 32 and 34 to the body portions.

The first cuff 32 is mounted for sliding movement on the first arm member 12 and is slidable along the first arm member 12 in a manner as described below. The second cuff 34 is mounted for sliding movement on a second arm member 14 and is slidable along the second arm member 12 in a manner as described below.

Bending a Joint in Extension:

In operation of the orthosis 10 to extend the joint, the orthosis 10 starts at a more flexed position. The first and second cuffs 32 and 34 are clamped onto the first and second body portions, respectively, by straps, tightly enough so that the cuffs 32 and 34 can apply torque to the body portions to extend the joint. The second arm member 14 is rotated from the first position to a second position, relative to the first arm member 12, rotating the second body portion about the joint axis 16 stretching the joint. As the second arm member 14 is rotated to the second position the second extension member 20 travels along an arcuate path about and substantially through point "P." The orthosis 10 is maintained in the second position for a predetermined treatment time providing a constant stretch to the joint.

As the orthosis 10 is rotated from the first position to the second position, extending the joint, the first and second cuffs 32 and 34 move along the first and second arm members 12 and 14. The first cuff 32 moves inwardly along the first arm member 12. Similarly, the second cuff 34 moves inwardly along the second arm member 14. Because the cuffs 32 and 34 are clamped onto the first and second body portions as described above, the outward pivoting movement of the first and second arm members 12 and 14 and the cuffs 32 and 34 causes the joint to be extended as desired. However, this extension of the joint can place strong distractive forces on the soft tissues around the joint. The sliding movement of the cuffs 32 and 34, inwardly along the first and second arm members 12 and 14, helps to limit these distractive forces by counteracting the outward movement of the first and second arm members 12 and 14. The cuffs 32 and 34 slide inwardly along the first and second arm members 12 and 14 a distance far enough so that the joint is only slightly distracted during extension. Thus, the detrimental effects of strong distractive forces normally generated in forced extension of a joint are avoided, being replaced with the beneficial effects of limited and controlled distraction.

Bending a Joint in Flexion:

In operation of the orthosis 10 to flex the joint, the orthosis 10 starts at a more extended position. The first and second cuffs 32 and 34 are clamped onto the first and second body portions, respectively, by straps, tightly enough so that the cuffs 32 and 34 can apply torque to the body portions to extend the joint. The second arm member 14 is rotated from the first position to a second position, relative to the first arm member 12, rotating the second body portion about the joint axis 16 stretching the joint. As the second arm member 14 is rotated to the second position the second extension member 20 travels about and substantially though point "P," along an arcuate path. The orthosis 10 is maintained in the second position for a predetermined treatment time providing a constant stretch to the joint.

As the orthosis 10 is rotated from the first position to the second position, flexing the joint the first and second cuffs 32 and 34 move along the first and second arm members 12 and 14. The first cuff 32 moves outwardly along the first arm member 12. Similarly, the second cuff 34 moves outwardly along the second arm member 14. Because the cuffs 32 and 34 are clamped onto the first and second body portions the inward pivoting movement of the first and second arm members 12 and 14 and the cuffs 32 and 34 causes the joint to be flexed as desired. However, this flexion of the joint can place strong compressive forces on the soft tissues around the joint. The sliding movement of the cuffs 32 and 34, outwardly along the first and second arm members 12 and 14, helps to limit these compressive forces by counteracting the inward movement of the first and second arm members 12 and 14. The cuffs 32 and 34 slide outwardly along the first and second arm members 12 and 14 a distance Far enough so that the joint is only slightly compressed during flexion. Thus, the detrimental effects of strong compressive forces normally generated in forced flexion of a joint are avoided, being replaced with the beneficial effects of limited and controlled compression.

Figure 9:
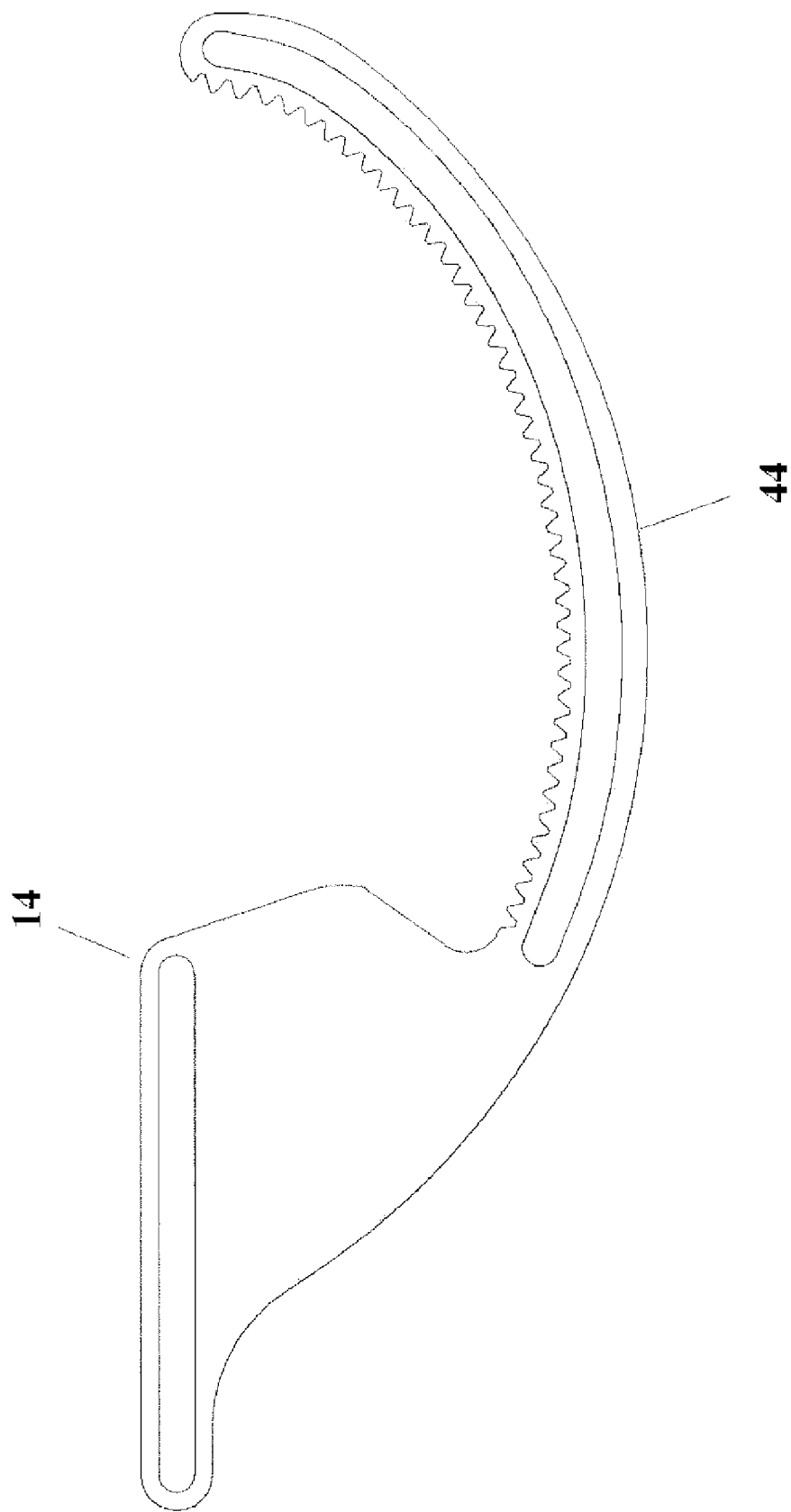
FIG. 9 shows a non-circular arcuate shaped second extension member of the present invention.

Referring to FIG. 9, the second arm member 14 is shown having a non-circular arcuate shaped second extension member 44. The non-circular arcuate shaped second extension member 44 provide an axis of rotation which changes as the second arm member 14 is moved from the first position to the second portion. As such, as the second arm member 14 is moved from the first position to the second portion the second body portion will exhibit both a rotational motion, about the joint axis 16, and a translational motion, distracting or compressing the joint.

Figure 10:
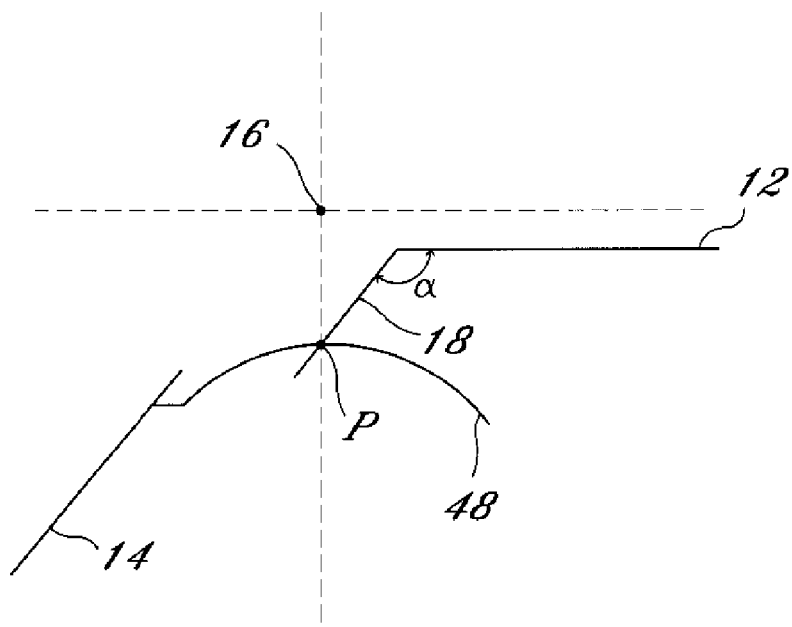
FIG. 10 shows an alternative arcuate shaped second extension member of the present invention.

In the previously described embodiments, the arcuate shape of the second extension member 20 or 44 as shown have concave radius of curvature relative to the joint 16. However, referring to FIG. 10, it is contemplated that the second extension member 20 or 44 can have a convex radius of curvature relative to the joint 16. Similar to the concave radius of curvature, the convex arcuate shape of the second extension member 20 or 44 results in the second body portion rotating about the joint axis 16, when the second arm member 14 is moved from a first position to a second position relative to the first arm member 12.

Figure 11:
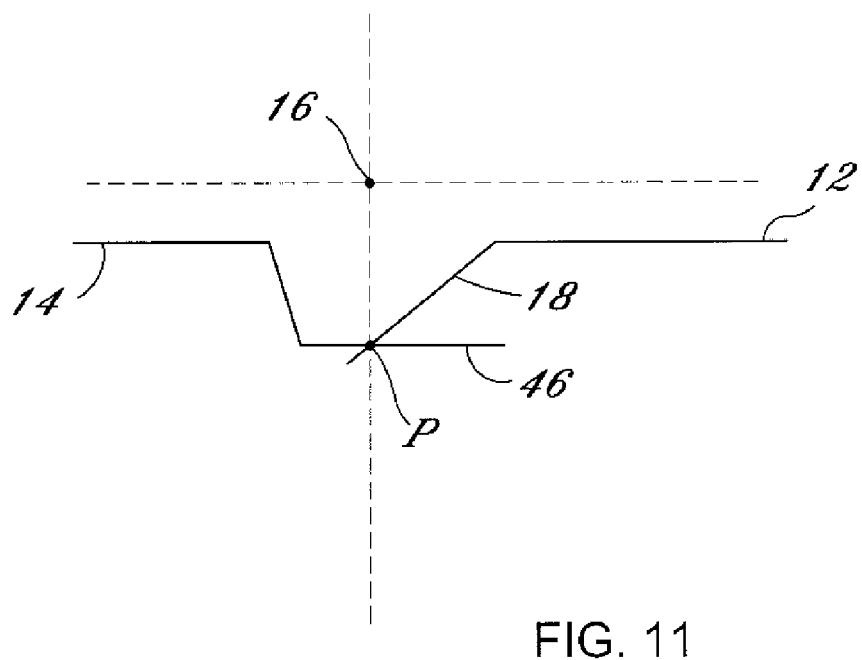
FIG. 11 shows a linear shaped second extension member of the present invention.

Referring to FIG. 11, the second arm member 14 of the orthosis 10 includes a second extension member 46 extending therefrom and having a linear shape. The first and second extension members 18 and 46 are operatively connected at point "P," such that in operation the second extension member 46 travels along a linear path through point "P." The linear shape of the second extension member 46 results in the second body portion being translated with respect to the first body portion. The translational movement of the second arm member 14 results in a distraction or compression of the joint when the second arm member 14 is moved from a first position to a second position relative to the first arm member 12.

As discussed further below, the hand pad can be mounted for translational and rotational movement on the base member.

Figure 12:
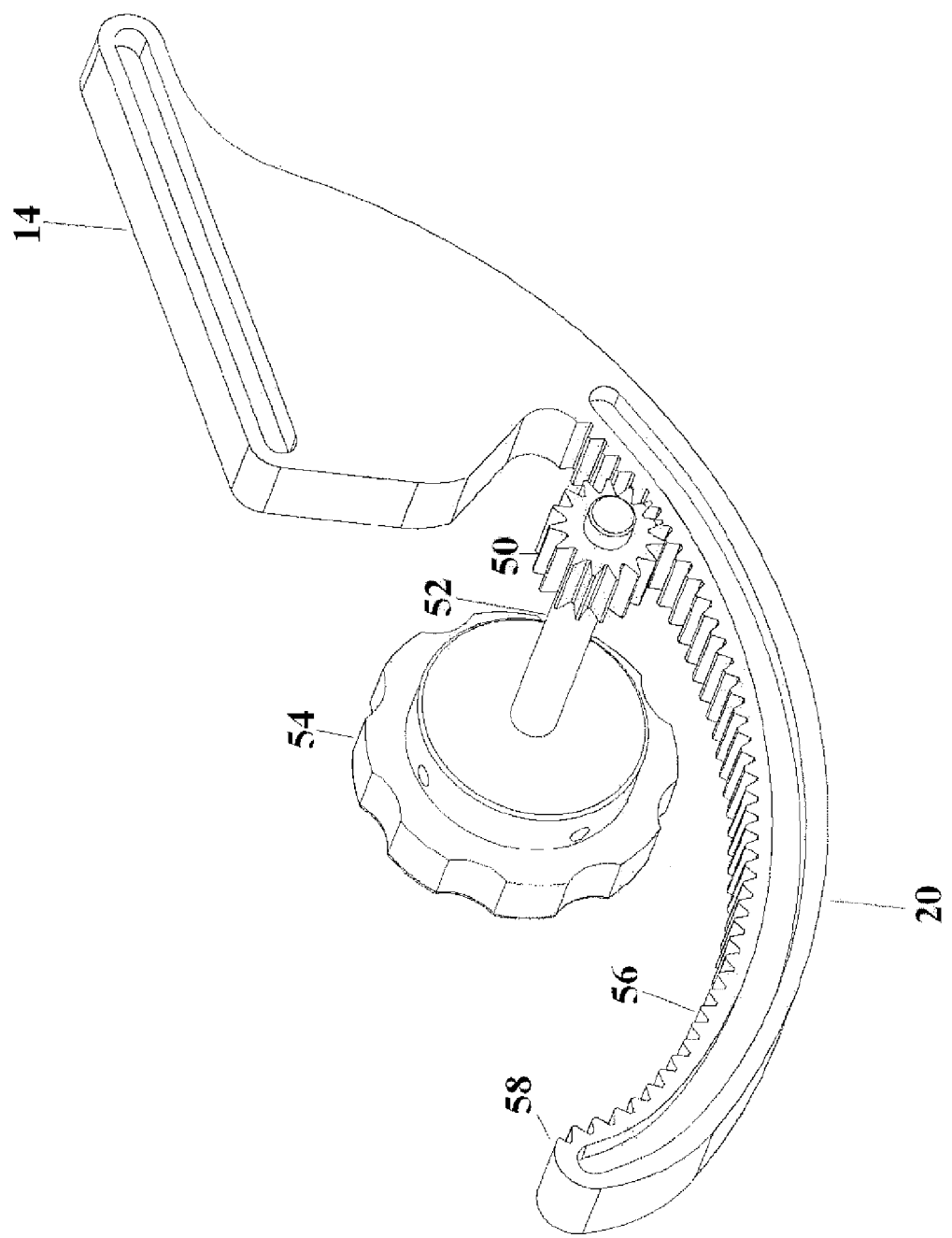
FIG. 12 shows an exemplary drive assembly of the present invention.

Drive Assembly:

Referring to FIG. 12, the drive assembly 22 of the orthosis includes a gear system. As previously noted, the components of the orthosis, including the drive assembly 22, can be made by injection molding a polymer. The drive assembly 22 is supported in the first extension member 18, including a gear 50 rotatable about point "P." A shaft 52, attached to the gear 50, extends from first extension member 18. A knob 54 is connected to the shaft 52, opposite the gear 50, for manually rotating the gear 50. The second extension member 20 includes a series of teeth 56 along an inner surface 58. The second extension member 20 is threaded through the first extension member 18, such that the teeth 56 on the second extension member 20 engage the gear 50. The rotation of the knob 56 causes the gear 50 to rotate, pushing or pulling the second extension member 20 through the first extension member 18. The drive assembly 22 includes a locking or breaking mechanism which prevents the gear 50 from rotating absent any applied Force rotation of the knob 56. Such a lock or breaking mechanism can include a compression washer or other known gear locking or breaking mechanisms.

The drive assembly 22 is described as utilizing a gear system. However, it is contemplated that other known drive systems can be used to move the second extension member 20 through the first extension member 18, for example a friction type drive system. Regardless of the drive system used, the joint orthosis of the present invention can act as a brace, restricting the relative movement of the first and second body portions to one degree of freedom (e.g. flexion and extension about the joint). Thus, drive assembly 22 can be configured to allow free motion in one degree of freedom. This can be achieved in a number of different ways. For example, gear 50 can be positioned such that it does not engage teeth 56.

In an alternative embodiment, the drive assembly 22 of orthosis 10 in accordance with the present invention can be actuated by a motor instead of by a manually actuatable member. Likewise, the motor may be configured an adapted with gearing that causes the orthosis to cycle through a range of motion in a predetermined manner, or alternatively maybe controlled by a programmable logic controller (PLC).

In an embodiment, an electric motor is mounted on the shaft 52 for rotation of the gear 50. A battery provides electric power to the motor. Alternatively, the motor can be supplied with external power. A microprocessor controls the operation of the motor. The microprocessor and motor together can be used to cycle the first and second arm members 12 and 14 through extension and flexion; to move the first and second arm members 12 and 14 in one pivotal direction a certain amount, hold there while tissue stretches, then move further in that direction; or in any other manner.

In another manner of use, the orthosis can be set to cycle to one end of the joint's range of motion and hold there for a predetermined period of time, then cycle to the other end of the joints range of motion and hold there. The programming and control of the microprocessor is within the skill of the art as it relates to driving the motor to control the first and second arm members 12 and 14 to move in known manners. This embodiment is ideally suited for continuous passive motion exercise, because the orthosis is portable and because the motor can be programmed with the desired sequence of movements.

It should be understood that the particular physical arrangement of the motor, the battery, and the microprocessor is not the only possible arrangement of those elements. The invention contemplates that other arrangements of these or similarly functional elements are quite suitable, and thus the invention is intended to cover any such arrangement. Additionally, another type of power source, other than an electric motor, can also be used. For example, the use of a hydraulic or pneumatic motor as the drive mechanism is contemplated.

Figure 13:
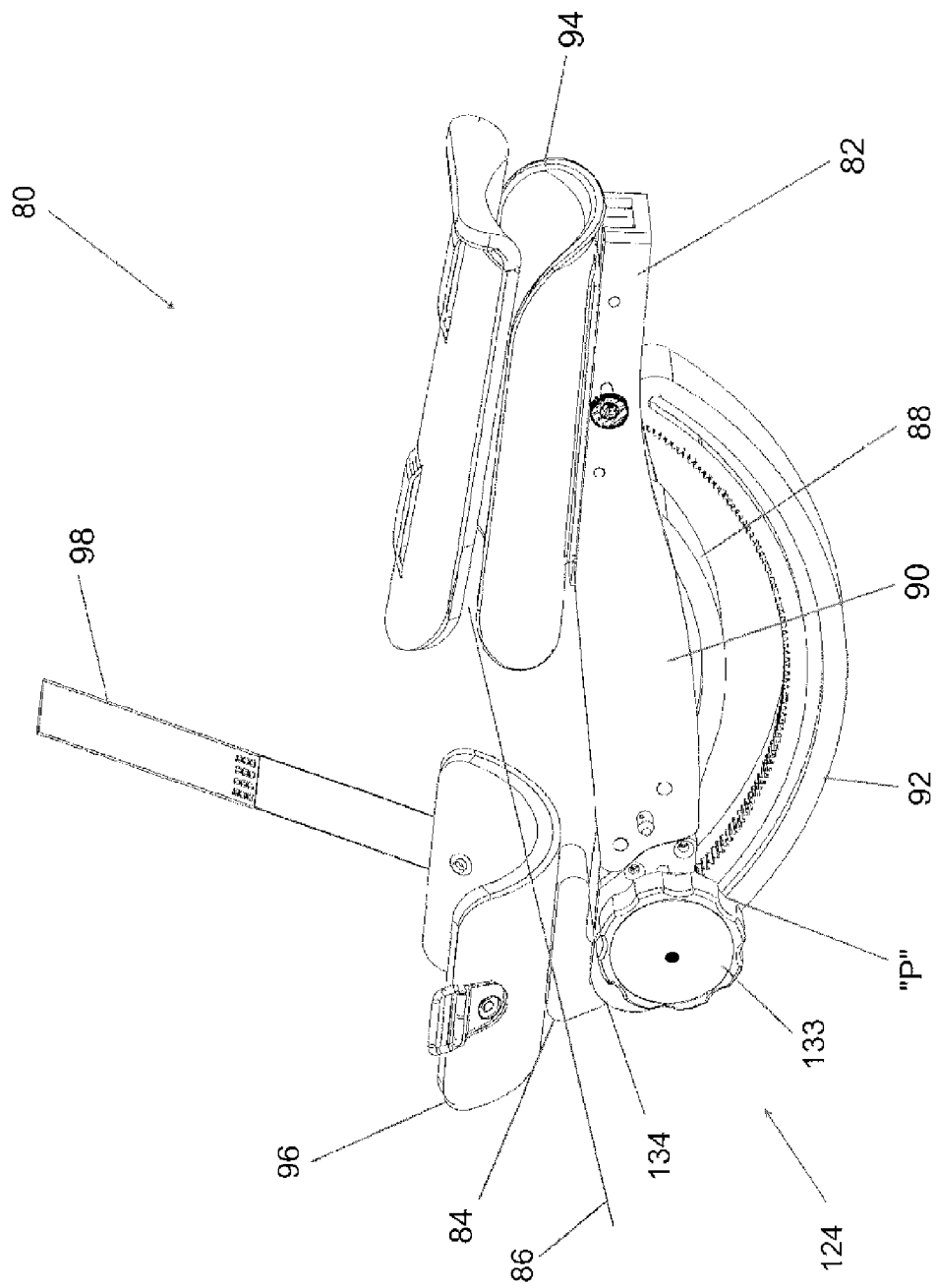
FIG. 13 depicts a first side view of another orthosis of the present invention for flexing and extending a joint in a patient.
Figure 14:
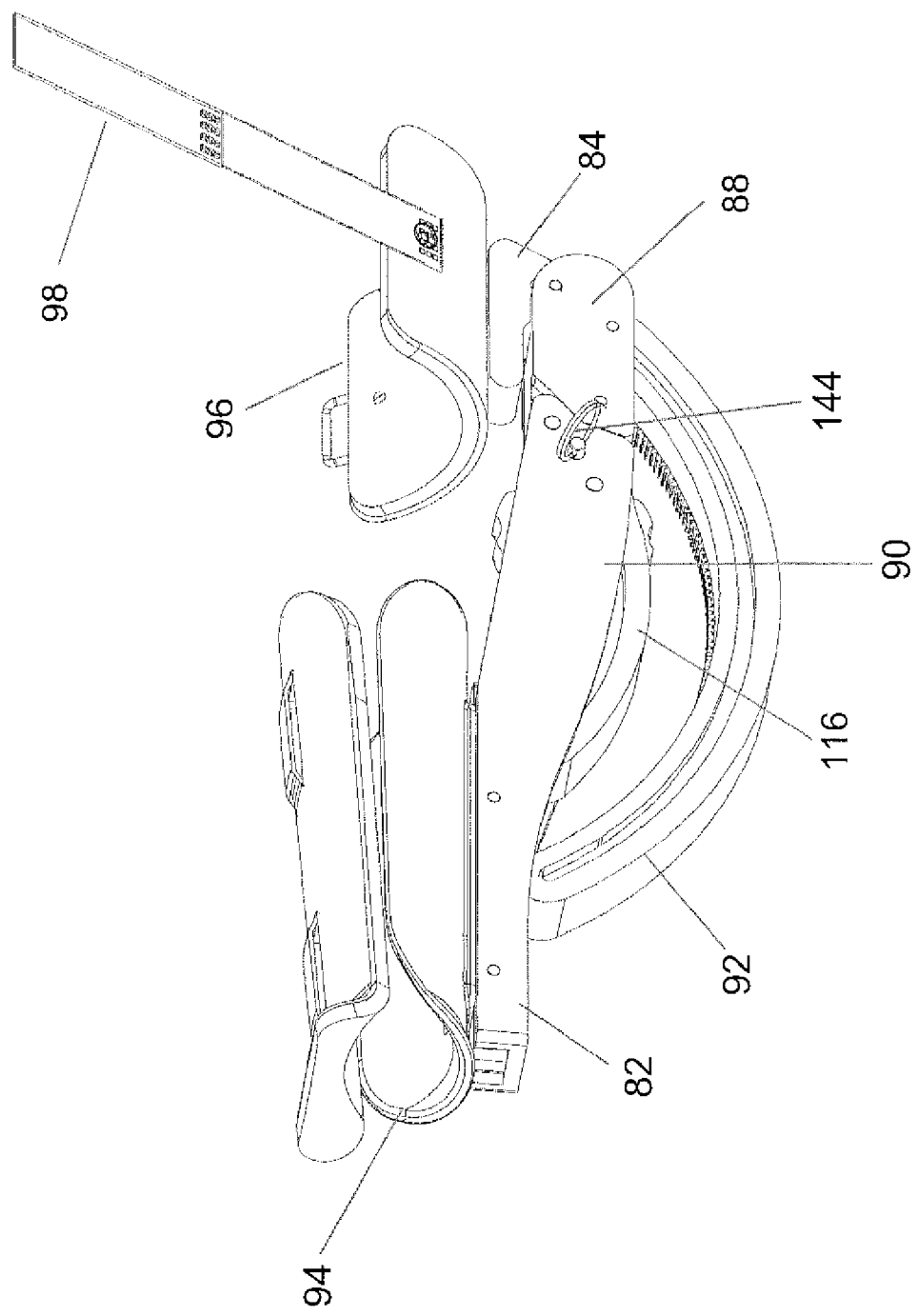
FIG. 14 depicts an opposite side view of the orthosis of FIG. 13.

Referring to FIGS. 13 and 14, an orthosis 80 of the present invention includes a first arm member 82 attachable to the first body portion and a second arm member 84 attachable to the second body portion, wherein the joint axis 86 is interposed between and offset from the first and second arm members 82 and 84. A third arm member 88 is interposed between the first and second arm members 82 and 84, where the first and second arm members 82 and 84 are connected to the third arm member 88, offset from the joint axis 86.

The first arm member 82 of the orthosis 80 includes a first extension member 90, which extends from the first arm member 82. The second arm member 84 of the orthosis 80 includes a second extension member 92 having an arcuate shape. The first and second extension members 90 and 92 are operatively connected to the third arm member 88, where the second extension member 92 is operably connected to the third arm member 88 at a point "P," such that in operation the third member 88 travels along an arcuate path of the second extension member 92. The arcuate shape of the second extension member 92 results in the first body portion rotating about the joint axis 86, when the first and third arm members 82 and 88 are moved from a first position to a second position relative to the second arm member 84. The radius of curvature of the second extension member 92 is a function of the joint to be treated and the degree of flexion or extension contractures.

A first cuff 94 is attached to the first arm member 82, wherein the first cuff 94 is positionable about the first body portion. The first cuff 94 is attached to the first body portion by cuff straps. The first cuff 94 secures the first body portion to the first arm member 82. A second cuff 96 is attached to the second arm member 84, wherein the second cuff 96 is positionable about the second body portion. The second cuff 96 is attached to the second body portion by a cuff strap(s) 98. The second cuff 96 secures the second body portion to the second arm member 84. The cuffs 94 and 96 can be provided in a variety of sizes or have adjustable sizes to fit about the body portions. (The term "cuff" as used herein means any suitable structure for transmitting the force of the orthosis 80 to the limb portion it engages.).

Figure 15:
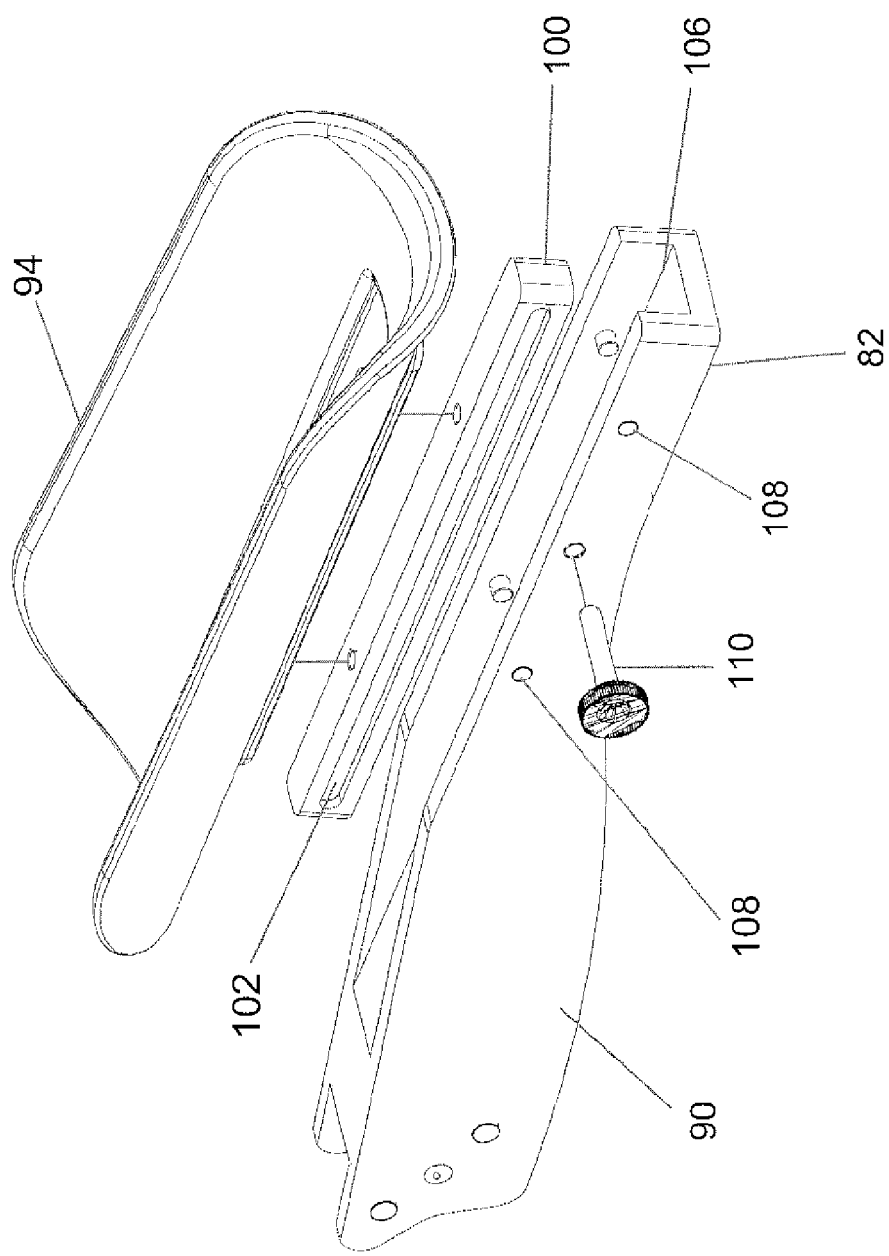
FIG. 15 depicts a first arm member of the orthosis of FIG. 13.

The first cuff 94 can be slidingly connected to the first arm member 82. Referring to FIG. 15, a sliding bar 100 is affixed to the first cuff 94. where the sliding bar 100 includes channels 102 positioned on opposite sides of the sliding bar 110. The first arm member 82 includes a main channel 106 configured to slidingly receive the sliding bar 100. Pins 108 are positioned though opposite sides of the main channel 106 of the first arm member 82 and into the channels 102 to slidingly secured the sliding bar 100 in the main channel 106. An adjustable member 110 can be threaded though the first arm member 82, into a channel 102 to adjustably secure the position of the sliding bar 102 in the main channel 106. As such, the position of the first cuff 94 can be adjusted with respected the first arm member 82, the position being secured with the adjustable member 110. Alternatively, the first cuff 94 can be free to slide with respect to the first arm member 82, thereby allowing the position of the first cuff 94 to self adjust during operation of the orthosis 80.

Similar to the first cuff 92, the second cuff 96 can be slidingly connected to the second arm member 84.

Figure 16:
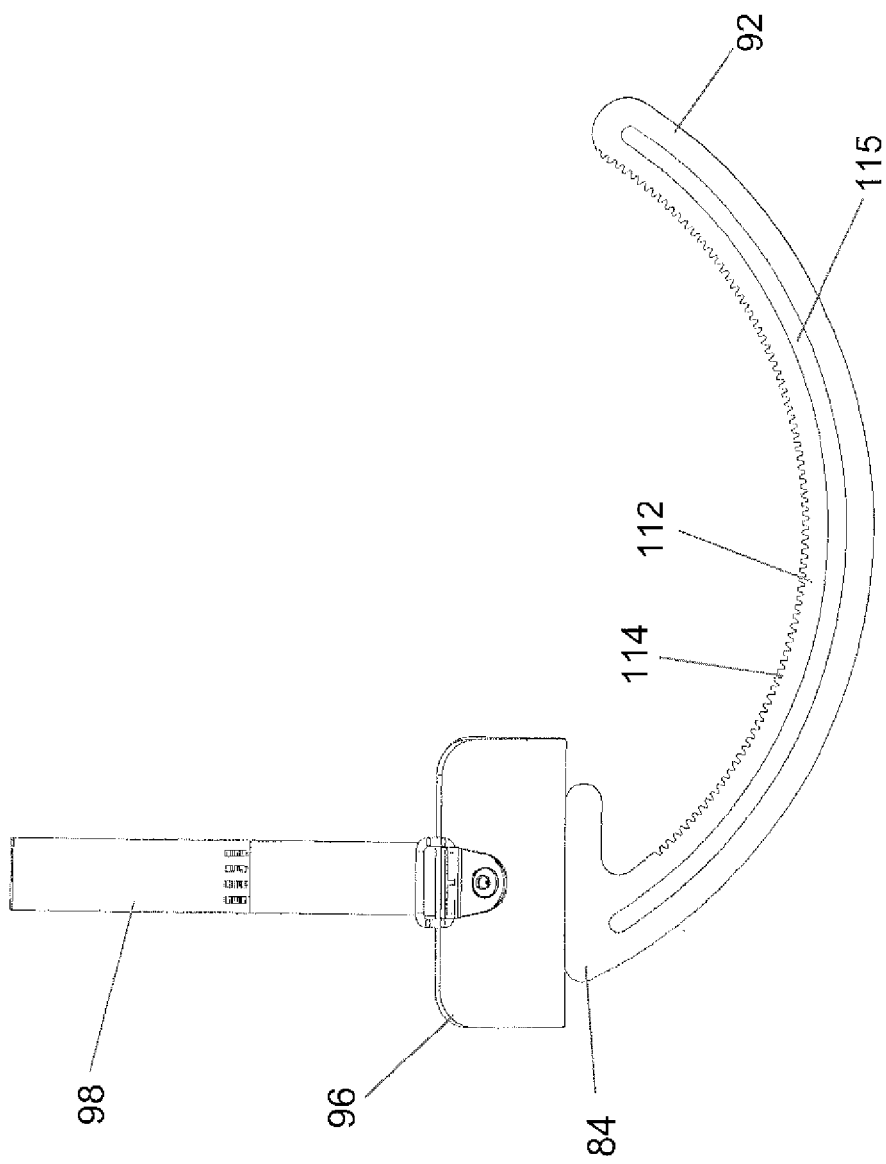
FIG. 16 depicts a second arm member of the orthosis of FIG. 13.

Referring to FIG. 16, the second extension member 92 has an arcuate shape, where the radius of curvature of the second extension member 92 is a function of the joint to be treated and the degree of flexion or extension contractures. The second extension member 92 includes an inner surface 112 have a plurality of teeth 114 thereon. The second extension member 92 can include channels 115 disposed on opposite sides thereof.

Figure 17:
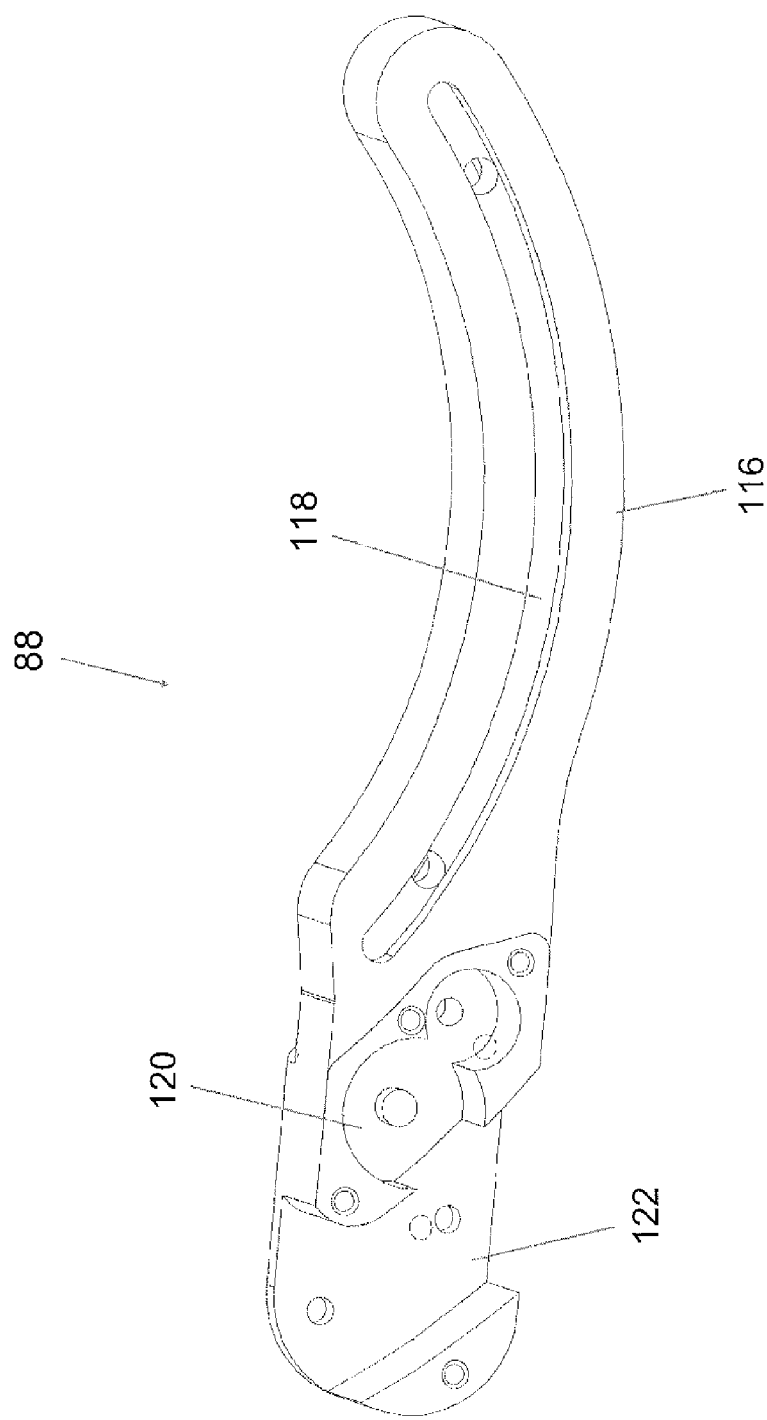
FIG. 17 depicts a third arm member of the orthosis of FIG. 13.

Referring to FIG. 17, the third arm member 88 includes a third extension member 116 has an arcuate shape, where the radius of curvature of the third extension member 116 is a function of the joint to be treated and the degree of flexion or extension contractures. The third extension member 116 includes channels 118 disposed on opposite sides thereof. A drive housing 120 is positioned proximal to a guide channel 122.

Figure 18:
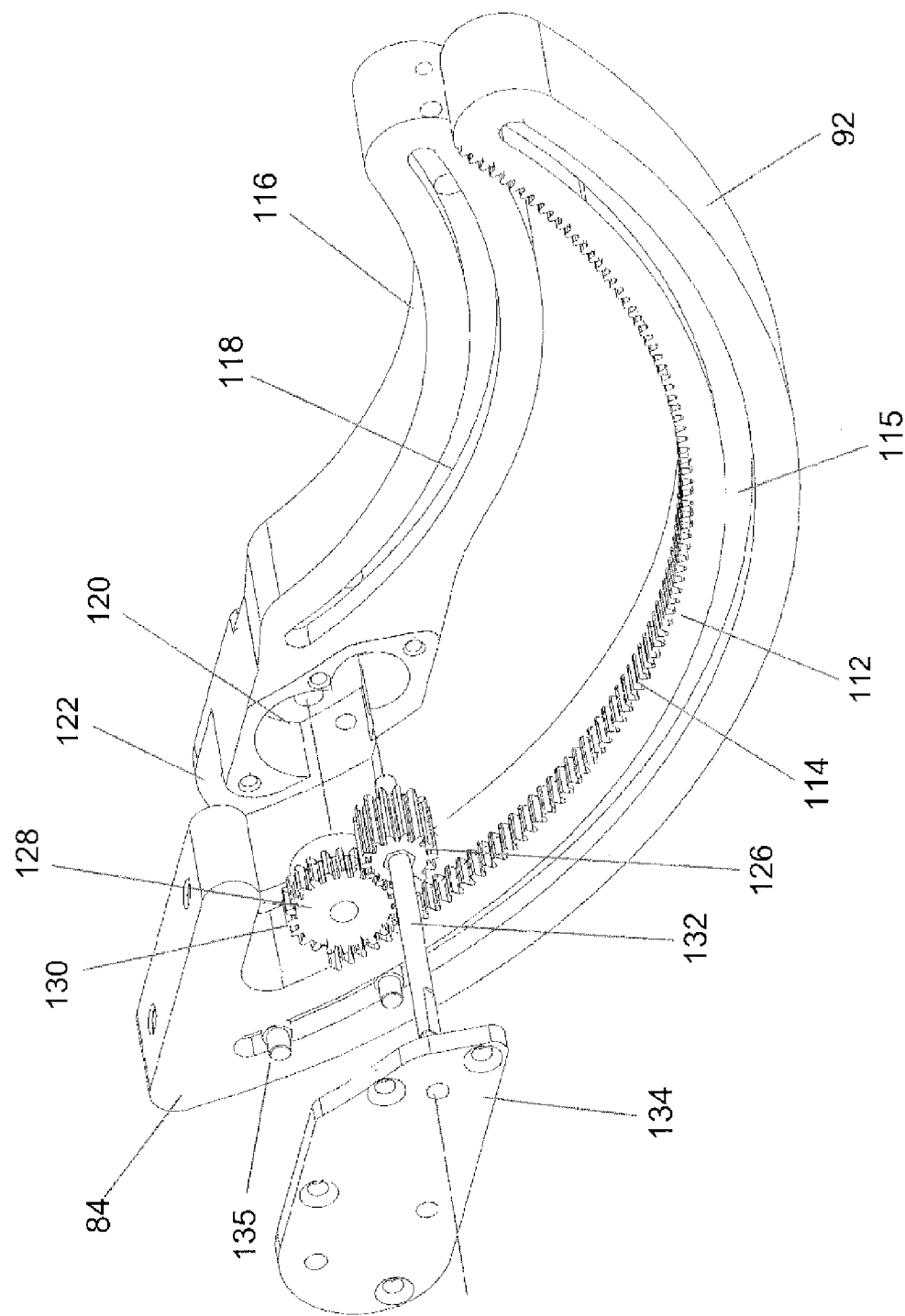
FIG. 18 depicts the drive assembly of the orthosis of FIG. 13.
Figure 19:
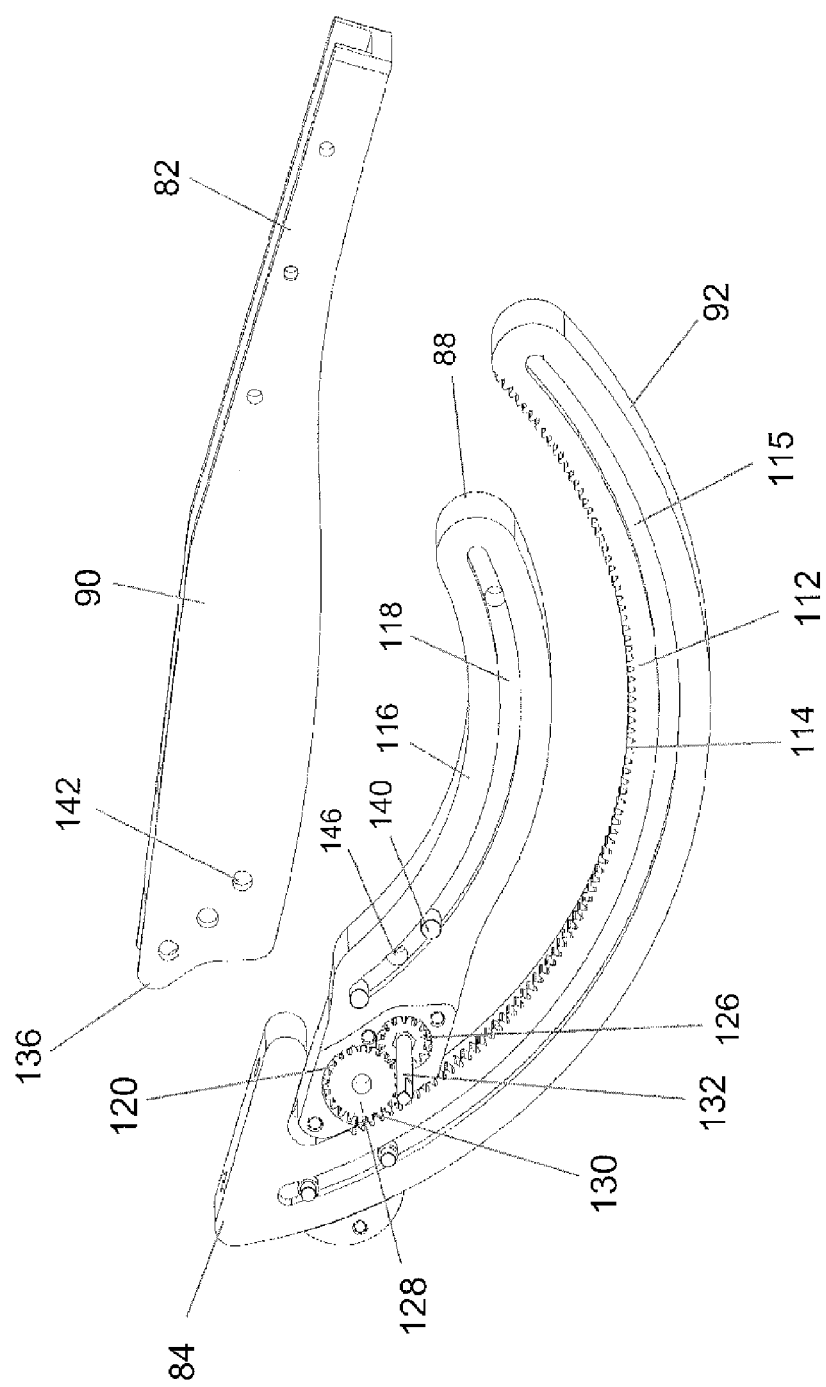
FIG. 19 depicts the connectivity of the first, second, and third arm members of the orthosis of FIG. 13.

Referring also to FIGS. 18 and 19, a drive assembly 124 is positioned in the drive housing 120 of the third arm member 88. The drive assembly 124 includes a drive gear 126 and a main gear 128, where the teeth of the drive gear 126 engage the teeth 130 of the main gear 128. A drive shaft 132 is connected to the drive gear 126, extending through the cover plate 134. A knob 133 can be affixed to the drive shaft 132 to facilitate rotation thereof. A rotation of the drive shaft 132 rotates the drive gear 126, which in turn rotates the main gear 128. The main gear 128 is sized such that a portion of the gear teeth 130 protrudes into the guide channel 122 of the third arm member 88.

The second extension member 92 is positioned in the guide channel 122, such that the gear teeth 132 of the main gear 128 engage the teeth 114 on the inner surface 112 of the second extension member 92. A rotation of the dive shaft 132 rotates the drive gear 126, which in turn rotates the main gear 128, driving the second extension member 92 through the guide channel 122. The cover plate 134 is positioned over the guide channel 122, securing the second extension member 92 in the guide channel 122 and defining a passage through which it travels.

Guide pins 135 can be positioned in the channels 115 of the second extension member 92, engaging on one side the third arm member 88 and on an opposite side the cover plate 134. The guide pins 135 can be used to secure the second extension member 92 in the passage and control the tacking of the third arm member 88 along the second extension member 92.

The drive mechanism 22 can further include a locking mechanism. The locking mechanism can be used to secure the position of the second arm member 84 with respect to the third arm member 88. The locking mechanism can prevent the actuation of the drive assembly 124, securing the position of second and third arm members 84 and 88. Alternatively, the locking mechanism can secure the second and third arm members 84 and 88, preventing an actuation of the drive mechanism 124 from moving the second and third arm members 84 and 88. The locking mechanism can be utilized such that the orthosis 80 can be used as a static splint.

The first arm member 82 can be sliding affixed to the third arm member 88. The first extension member 90 is positioned about the third extension member 88, where an end portion 136 of the first extension member 90 is slidingly connected about the third extension member 118. Pins 140 are positioned through pin holes 142, provided on opposite sides of the end portion 136 of the first extension member 90, into the channels 118 of the third extension member 88, thereby allowing the end portion 136 of the first extension member 90 to slide along the arcuate path defined by the channels 118, rotating the first arm member 82 about the joint axis 86. The first arm member 82 can slide freely with respect to the third extension member 116. Alternatively, a push pin 144 can be positioned through the end portion 136 of the first extension member 92 into push pin hole 146 in the channels 118 of the third extension member 116. (See also FIG. 14). The push pin 144 prevents relative movement of the first arm member 82 with respect to the third arm member 88.

In an exemplary use, the orthosis 80 is operated to extend a joint in the following manner. The first cuff 94 is fastened about the first body portion tightly enough that the first arm member 82 may apply torque to the first body portion without having the first cuff 94 slide along the first body portion. Similarly, the second cuff 96 is fastened securely around the second body portion so that the second arm member 84 may apply torque to the second body portion without the second cuff 96 sliding along the second body portion. The orthosis 80 is attached to the first and second body portions in a first position. The first and second arm members 82 and 84 are rotated from the first position to a second position, relative to the second arm member 84, rotating the first body portion about the joint axis 86 stretching the joint. As the first and second arm members 82 and 84 are rotated to the second position, the third arm member 88 travels along an arcuate path along the second extension member 92. The orthosis 80 is maintained in the second position for a predetermined treatment time providing a constant stretch to the joint. Additionally, the second extension member 92 can be made of a substantially rigid but flexible material, such that while the first arm member 82 is in the second position the second extension member 92 acts like a spring, providing dynamic stretch to the connective tissue of the joint.

After the expiration of the treatment time, the first arm member 82 is moved back to the first position, relieving the joint. Optionally, the first arm member 82 can be rotated to a third position, increasing the stretch on the joint. The first arm member 82 can be rotated at discrete time intervals to incrementally increase the stretch of the joint through the treatment cycle. After completion of the treatment cycle, the first arm member 82 is returned to the first position for removal of the orthosis 80.

In another exemplary use, the push pin 144 is removed from the first and third arm members 82 and 88, such that as the first and third arm members 82 and 88 are moved from a first position to a second position, with respected to the second arm member 84, the first arm member 82 can slide along the arcuate path of the third extension 116 of the third arm member 88. This can be utilized to increase the range on motion of the orthosis 80. It is contemplated that the orthosis 80 can have a range of motion from around 15 degrees to around 145 degrees.

The first, second, and third arm members 82, 84, and 88 are rigid members made oft for example, aluminum, stainless steel, polymeric, or composite materials. The arms are rigid so as to be able to transmit the necessary forces. It should be understood that any material of sufficient rigidity can be used.

In an embodiment, the components of the orthosis 80 of the present invention are made by injection molding. Generally for injection molding, tool and die metal molds of the orthosis 80 components are prepared. Hot, melted plastic material is injected into the molds. The plastic is allowed to cool, forming components. The components are removed from the molds and assembled. The cuff portions 92 or 96 can be individual molded and attached to the arm members 82 or 84. Alternatively, the cuff portions can be molded as an integrated pant of the arm members 82 or 84.

Similarly, the gears 132 and 134 are rigid members made of, for example, aluminum, stainless steel, polymeric, or composite materials. The gears 132 and 134 are rigid so as to be able to transmit the necessary forces.

Bending an Elbow Joint Flexion:

In operation of the orthosis 80 to flex an elbow joint, the orthosis 80 starts at a more extended position. The first and second cuffs 94 and 96 are clamped onto the forearm and bicep portions of the arm, respectively, by straps, tightly enough so that the cuffs 94 and 96 can apply torque to the body portions to flex the joint. The first and second arm members 82 and 84 are rotated from the first position to a second position, relative to the second arm member 84, rotating the forearm about the elbow joint axis 86 stretching the joint. As the first and second arm members 82 and 84 are rotated to the second position the third arm member 88 travels along the arcuate path of the second extension member 92. The orthosis 80 is maintained in the second position for a predetermined treatment time providing a constant stretch to the joint.

Figure 20:
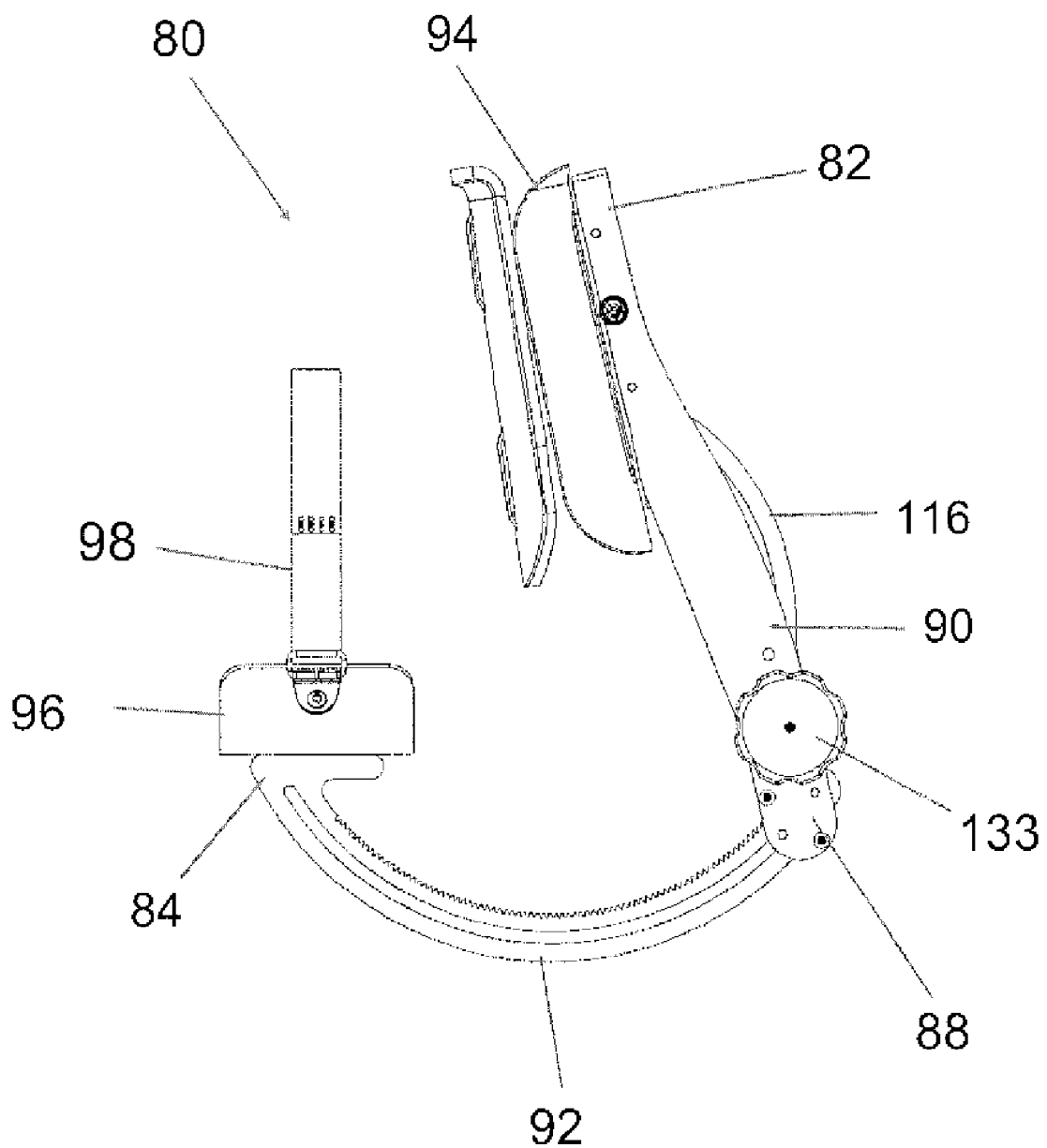
FIG. 20 depicts the orthosis of FIG. 13 in a middle flexed position.

After the expiration of the treatment time, the first and second arm members 82 and 884 are moved back to the first position, relieving the joint. Optionally, the first and second arm members 82 and 84 can be rotated to a third position, increasing the stretch on the joint. The first and second arm members 82 and 84 can be rotated at discrete time intervals to incrementally increase the stretch of the joint through the treatment cycle. Referring to FIG. 20, the treatment cycle can continue until the third arm member 88 traverses the second extension member 82. After completion of the treatment cycle, the first and second arm members 82 and 84 are returned to the first position for removal of the orthosis 80.

Figure 21:
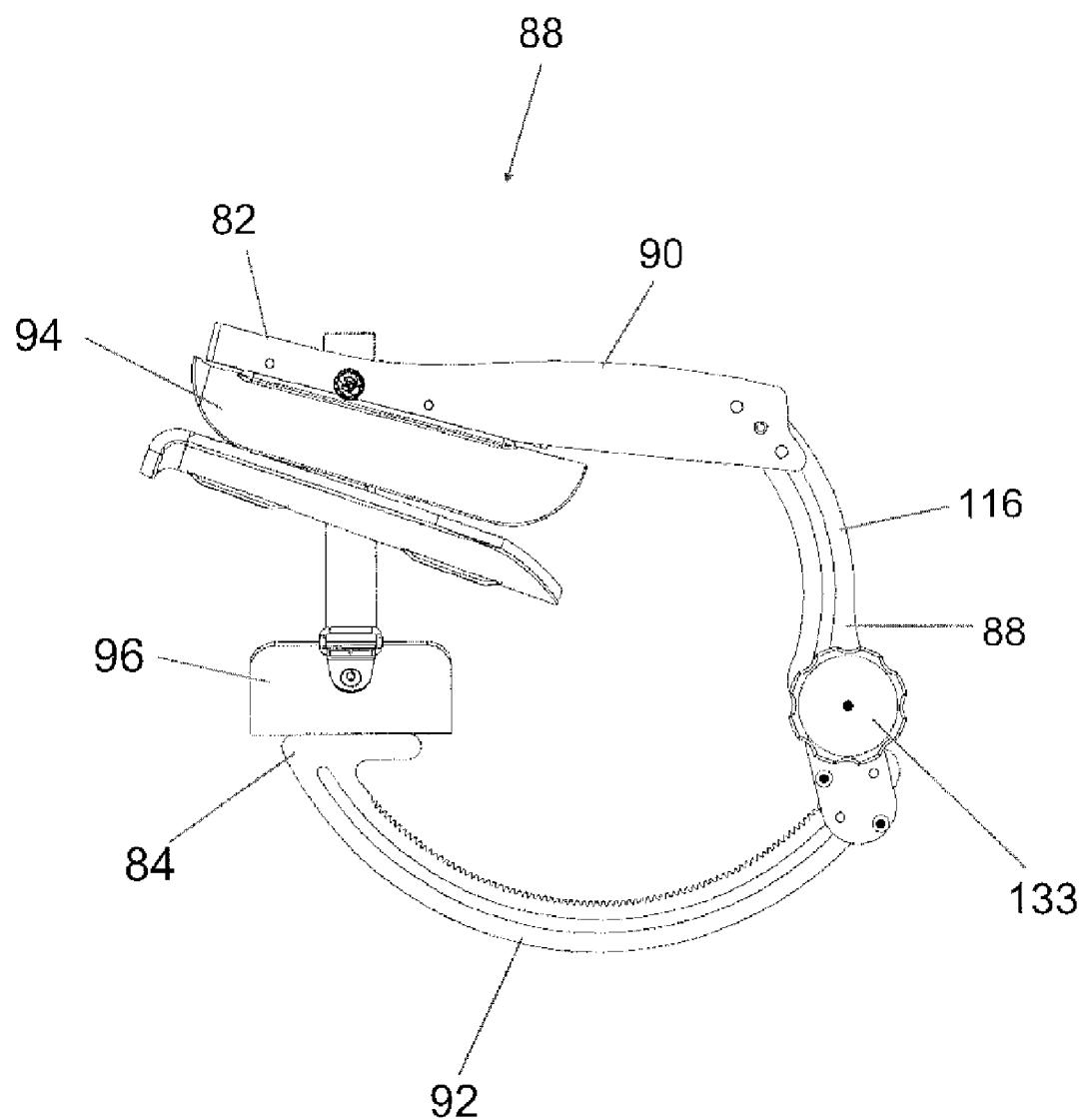
FIG. 21 depicts the orthosis of FIG. 13 in a fully flexed position.

Alternatively, the first arm member 82 can be released to move along the third arm member 88. Referring to FIG. 21, the first and third arm members 82 and 88 are rotated from the first position to a second position, relative to the second arm member 84, rotating the forearm about the joint axis 86 stretching the joint. As the third arm member 88 is rotated to the second position, the first arm member 82 can travel along an arcuate path of the third extension member 116, thereby increasing the range of motion.

Bending an Elbow Joint in Extension:

When an elbow joint is to be bent in extension, the first cuff 94 is connected with the forearm and the second cuff 96 is connected to the bicep. The first and second cuffs 94 and 96 are clamped onto the forearm and biceps respectively, by straps, tightly enough so that they can apply torque to flex the joint. The first and third arm members 82 and 88 are rotated from the first position to a second position, relative to the second arm member 84, rotating the forearm about the elbow joint axis 86 stretching the joint. As the first and third arm members 82 and 88 are rotated to the second position the third arm member 88 travels along the arcuate path of the second extension member 92. The orthosis 80 is maintained in the second position for a predetermined treatment time providing a constant stretch to the joint.

After the expiration of the treatment time, the first and second arm members 82 and 84 are moved back to the first position, relieving the joint. Optionally, the first and second arm members 82 and 84 can be rotated to a third position, increasing the stretch on the joint. The first and second arm members 82 and 84 can be rotated at discrete time intervals to incrementally increase the stretch of the joint through the treatment cycle. After completion of the treatment cycle, the first and second arm members 82 and 84 are returned to the first position for removal of the orthosis 80.

Alternatively, the first arm member 82 can be released to move along the third arm member 88. The first and third arm members 82 and 88 are rotated from the first position to a second position, relative to the second arm member 84, rotating the second body portion about the joint axis 86 stretching the joint. As the third arm member 88 is rotated to the second position, the first arm member 82 can travel along an arcuate path of the third extension member 116, thereby increasing the range of motion.

In the above description, the second and/or third extension members 92 and 116 are shown and described as having a substantially circular arcuate shape, positioning the axis of rotation at the joint axis 86. However, it is contemplated that the second and/or third extension members 92 and 116 can have alternative shapes.

The drive assembly 124 is described as utilizing a gear system. However, it is contemplated that other known drive systems can be used to move the first extension member 90 with respect to the second extension member 92 for example a friction type drive system. Regardless of the drive system used, the joint orthosis of the present invention can act as a brace, restricting the relative movement of the first and second body portions to one degree of freedom (e.g. flexion and extension about the joint). Thus, drive assembly 124 can be configured to allow free motion in one degree of freedom. This can be achieved in a number of different ways. For example, gear 128 can be positioned such that it does not engage teeth 130.

In an alternative embodiment, the drive assembly 124 of orthosis 80 in accordance with the present invention can be actuated by a motor instead of by a manually actuatable member, such as the knob 133. Likewise, the motor may be configured and adapted with gearing that causes the orthosis to cycle through a range of motion in a predetermined manner, or alternatively maybe controlled by a programmable logic controller (PLC).

In an embodiment, an electric motor is mounted to the shaft 132 for rotation of the gear 128. A battery provides electric power to the motor. Alternatively, the motor can be supplied with external power. A microprocessor controls the operation of the motor. The microprocessor and motor together can be used to cycle the second and third arm members 84 and 88 through extension and flexion; to move the first and second arm members 82 and 84 in one pivotal direction a certain amount, hold there while tissue stretches, then move further in that direction; or in any other manner.

In another manner of use, the orthosis can be set to cycle to one end of the joint's range of motion and hold there for a predetermined period of time, then cycle to the other end of the joints range of motion and hold there. The programming and control of the microprocessor is within the skill of the art as it relates to driving the motor to control the second and third arm members 84 and 88 to move in known manners. This embodiment is ideally suited for continuous passive motion exercise, because the orthosis is portable and because the motor can be programmed with the desired sequence of movements.

It should be understood that the particular physical arrangement of the motor, the battery, and the microprocessor is not the only possible arrangement of those elements. The invention contemplates that other arrangements of these or similarly functional elements are quite suitable, and thus, the invention is intended to cover any such arrangement. Additionally, another type of power source, other than an electric motor, can also be used. For example, the use of a hydraulic or pneumatic motor as the drive mechanism is contemplated.

The present invention can further include a monitor for use with the orthosis 10, 80, which provides assurances the patient is properly using the orthosis 10, 80 during his/her exercise period. For instance, the monitor can have a position sensor, a temperature sensor, a force sensor, a clock or timer, or a device type sensor for monitoring the patient's implementation of a protocol. The information obtained from these monitoring devices may be stored for later analysis or confirmation of proper use or may be transmitted in real-time during use of the device. The data obtained from the monitor can be analyzed by a healthcare professional or technician and the protocol can be adjusted accordingly.

This analysis may be conducted remotely, thereby saving the time and expense of a home visit by a healthcare professional or technician. An exemplary monitoring system is provided in U.S. Pat. No. 7,182,738 entitled "Patient Monitoring Apparatus and Method for Orthosis and Other Devices," to Bonutti et al., the content of which is herein expressly incorporated by reference in its entirety.

The components of the present invention are rigid members made of, for example, aluminum, stainless steel, polymeric, or composite materials. The member and extensions are sufficiently rigid to transmit the necessary forces. It should be understood that any material of sufficient rigidity might be used, For example, some components can be made by injection molding. Generally, for injection molding, tool and die metal molds of the components are prepared. Hot, melted plastic material is injected into the molds. The plastic is allowed to cool, forming components. The components are removed from the molds and assembled.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally, the device can be made of a nonmagnetic material. In such instance, the device can be used as a positioning device for use in imaging devices, such as a MRI device. It is also contemplated that the device can be used as a positioning device for use during surgical procedures, where it may be necessary to adjust and hold the position of the joint.

It will be appreciated by persons skilled in the art that the present invention is not limited to what has been particularly shown and described herein above. For example, although the examples presented identify the wrist joint, the present invention can be used for any joint. In addition, unless mention was made above to the contrary, it should be noted that all of the accompanying drawings are not to scale. A variety of modifications and variations are possible in light of the above teachings without departing from the scope and spirit of the invention.

What is claimed:

1. An orthosis for stretching tissue around a joint of a patient connecting a first body portion and a second body portion, the orthosis comprising:
    a first arm member for coupling to the first body portion including at least a curved portion; and
    a second arm member for coupling to the second body portion, the second arm member operatively coupled to the first arm member and movable with respect to a length of the curved portion;
    wherein at least one of the first and second body portions is rotated about an axis of rotation of the joint and each of the first arm member and the second arm member is offset with respect to the axis of rotation of the joint.

2. An orthosis in accordance with claim 1 wherein the curved portion includes an arcuate portion and a first end of the second arm member is movable along the length of the arcuate portion.

3. An orthosis in accordance with claim 1 wherein the first and second arm members are positioned substantially within an orthosis plane.

4. An orthosis in accordance with claim 3 wherein the orthosis plane is substantially orthogonal to the axis of rotation of the joint.

5. An orthosis in accordance with claim 1 wherein the first arm member comprises an extension member movably coupled to the first arm member and configured to at least one of increase and decrease a range of motion of the orthosis.

6. An orthosis in accordance with claim 1 wherein the second arm member moves along an arcuate path defined by the first arm member.

7. An orthosis in accordance with claim 1 further comprising a drive assembly operatively coupled to the second arm member.

8. An orthosis in accordance with claim 7 wherein the drive assembly comprises a gear rotatably mounted on the first arm member.

9. An orthosis in accordance with claim 8 wherein the gear is manually rotatable for selectively moving the second arm member with respect to the first arm member.

10. An orthosis in accordance with claim 7 wherein the first arm member comprises a plurality of teeth formed on the curved portion for engaging the gear.

11. An orthosis in accordance with claim 7 wherein the drive assembly comprises a motor.

12. An orthosis in accordance with claim 7 wherein the drive assembly comprises a locking assembly.

13. An orthosis in accordance with claim 1 wherein at least a portion of at least the second arm member comprises a flexible portion configured to dynamically stretch the tissue.

14. An orthosis in accordance with claim 1 further comprising a spring member connected to at least the second arm member for dynamically stretching the tissue.

15. A method of assembling an orthosis for stretching tissue around a joint of a patient connecting a first body portion and a second body portion, the method comprising:
    configuring a first arm member to couple to the first body portion, at least a portion of the first arm member positioned within an orthosis plane and having at least a curved portion; and
    operatively coupling a second arm member to the first arm member, the second arm member configured to couple to the second body portion, the second arm member movable within the orthosis plane with respect to a length of the curved portion to rotate the second body portion about an axis of rotation of the joint.

16. A method of assembling an orthosis in accordance with claim 15 wherein coupling the second arm member to the second body portion comprises moveably coupling the second arm member to the first arm member such that a first end of the second arm member is movable along the length of the curved portion.

17. A method of assembling an orthosis in accordance with claim 15 wherein coupling the second arm member comprises providing the second arm member configured to move along an arcuate path defined by the first arm member.

18. A method of assembling an orthosis in accordance with claim 15 further comprising operatively coupling a drive assembly to the first arm member and to the second arm member.

19. A method of assembling an orthosis in accordance with claim 18 further comprising coupling a motor to the drive assembly.

20. A method of assembling an orthosis in accordance with claim 18 further comprising providing the drive assembly that includes a locking assembly.

21. A method of assembling an orthosis in accordance with claim 15 wherein a gear is rotatably mounted on the first arm member.

22. A method of assembling an orthosis in accordance with claim 21 further comprising engaging the gear with a plurality of teeth formed on the curved portion of the first arm member.

23. A method of assembling an orthosis in accordance with claim 21 further comprising rotatably mounting the gear on the first arm member.

24. An orthosis in accordance with claim 15 wherein at least a portion of at least the second arm member comprises a flexible portion configured to dynamically stretch the tissue.

25. An orthosis in accordance with claim 15 further comprising a spring member connected to at least the second arm member for dynamically stretching the tissue.

26. An orthosis for stretching tissue around a joint of a patient connecting a first body portion and a second body portion, the orthosis comprising:
    a first arm member for coupling to the first body portion and defining a curved path;
    a second arm member for coupling to the second body portion and operatively coupled to the first arm member, the second arm member movable along the curved path, to rotate the second body portion about an axis of rotation of the joint; and
    an extension member movably coupled to the first arm member, wherein the extension member is configured to at least one of increase and decrease a range of motion of the orthosis.

27. An orthosis in accordance with claim 26 wherein at least a portion of the curved path includes an arcuate path.

28. An orthosis in accordance with claim 26 wherein a first end of the second arm member is selectively movable along the curved path to rotate the second body portion about the axis of rotation of the joint.

29. An orthosis in accordance with claim 26 wherein the first arm member is positioned within an orthosis plane substantially orthogonal to the axis of rotation of the joint.

30. An orthosis in accordance with claim 26 further comprising a drive assembly operatively coupled to the second arm member.

31. An orthosis in accordance with claim 30 wherein the drive assembly comprises a gear rotatably mounted on the first arm member.

32. An orthosis in accordance with claim 26 wherein at least a portion of at least the second arm member comprises a flexible portion configured to dynamically stretch the tissue.

33. An orthosis in accordance with claim 26 further comprising a spring member connected to at least the second arm member for dynamically stretching the tissue.

\* \* \* \* \*